(12) United States Patent
Raheja et al.

(10) Patent No.: US 10,510,130 B2
(45) Date of Patent: Dec. 17, 2019

(54) MOBILE DEVICE TASK MANAGEMENT AND QUEUE FOR MEDICAL TRIAGE

(71) Applicant: Charu Software Solutions, Jacksonville, FL (US)

(72) Inventors: Charu G. Raheja, Winston-Salem, NC (US); Ravi K. Raheja, Nashville, TN (US)

(73) Assignee: Charu Software Solutions, Jacksonville, FL (US)

( * ) Notice: Subject to any disclaimer, the term of this patent is extended or adjusted under 35 U.S.C. 154(b) by 1072 days.

(21) Appl. No.: 14/610,520

(22) Filed: Jan. 30, 2015

(65) Prior Publication Data

US 2015/0221057 A1    Aug. 6, 2015

Related U.S. Application Data

(60) Provisional application No. 61/934,522, filed on Jan. 31, 2014.

(51) Int. Cl.
| | | |
|---|---|---|
| *G06Q 50/00* | (2012.01) | |
| *G06Q 50/22* | (2018.01) | |
| *G06Q 10/06* | (2012.01) | |
| *G06Q 10/00* | (2012.01) | |

(52) U.S. Cl.
CPC ....... *G06Q 50/22* (2013.01); *G06Q 10/06311* (2013.01)

(58) Field of Classification Search
CPC ........... A61N 1/08; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06Q 10/10; G06Q 40/08; G06Q 50/22; G06Q 50/24; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30; G16H 50/50; G16H 50/70; G16H 50/80; G16H 70/00; G16H 70/20; G16H 70/40; G16H 70/60; G16H 70/80

See application file for complete search history.

(56) References Cited

U.S. PATENT DOCUMENTS

| | | | |
|---|---|---|---|
| 2010/0070296 A1* | 3/2010 | Massoumi | G06Q 10/10 705/2 |
| 2014/0019162 A1* | 1/2014 | Skowronski | G06F 19/322 705/3 |

* cited by examiner

*Primary Examiner* — Tran N Nguyen
(74) *Attorney, Agent, or Firm* — Schwegman Lundberg & Woessner, P.A.

(57) ABSTRACT

This document discusses, among other things, systems and methods for preventing fraud in remote service inquiries in medical and other environments. An individual may be able to register only one device per profile. The doctor approves each patient and the device prior to the patient being allowed to call a phone number associated with the nursing triage service. When the caller uses that device, the teller is able to confirm that the register device is associated with the patient. This provides an additional layer of security without requiring caller to identify the phone number.

20 Claims, 5 Drawing Sheets

MOBILE DEVICE TASK MANAGEMENT AND QUEUE FOR MEDICAL TRIAGE

RELATED APPLICATIONS

This application claims the benefit of priority to U.S. Provisional Patent Application Ser. No. 61/934,522, filed Jan. 31, 2014, which is incorporated herein by reference in its entirety.

TECHNICAL FIELD

This patent document pertains generally to website and mobile device task management and queue systems and methods and more particularly, but not by way of limitation, to such computer-assisted systems, such as for medical inquiry triage or call center management such as for businesses with product or service offerings.

BACKGROUND

Efficient and accurate handling of customer inquiries is particularly important in medical applications, such as for hospitals and clinics. One issue affecting medical applications is prevention of abuse of medical coverage. In examples where an external party pays for remotely provided medical coverage, there is potential for abuse when a covered individual shares access to the remotely provided medical coverage with individuals not covered by the system. In situations where the coverage is provided by telephone, a caller needs to call a teller, and the teller asks private questions that only the caller would know to confirm the caller's identity. However, current implementations may not be able to prevent a caller not covered by a medical policy from pretending to be a medically covered individual. This may occur because the covered party has little incentive to prevent abuse of the request, such as allowing others to use the service in the name of the covered party.

Fraud may also occur using nurse triage phone lines than have been preauthorized by a physician, a medical managed company, a corporation, or other entity. In some existing configurations, the care provider may forward their own patient's phone calls to an outsourced nurse triage. Currently, when a patient calls, the nurse evaluates the patient's symptoms and decides on the required level of care for the patient using medical protocols. The nurse then relays the information about the call to the physician or the paying party so that the paying party may follow up if needed. The physician receives information about the patient phone call and the disposition given to the patient by the nurse. Because the nurse-patient interaction occurs by phone, it is possible that additional callers could use the line, even callers who are not patients of the doctor or covered by the managed care policy or corporate policy. This abuse of nurse lines could become a significant issue if patients could easily request a phone call directly to a nurse without having to make a phone call, such as by using a website or using a mobile electronic device application such as on a smartphone or tablet.

Some existing solutions for prevention of fraud in medical request submissions often include placing a phone call to a nurse to verify information and route the request. Once routed, a medical practitioner may return the phone call to the client to discuss the medical request. Another existing solution includes the user logging into an electronic web portal, submitting a description of the medical request, and requesting a return phone call to address the medical request. However, submitting a medical request return call via an electronic web portal operates similar to leaving a generalized voicemail message, where the message does not result in an immediate response. Unlike phone call to a nurse that may be prioritized or routed according to the urgency of the request, an electronic web portal request routes the return call request into the general electronic medical record, which may not be prioritized or routed until the medical practitioner returns the call and discusses the medical request.

OVERVIEW

The present inventors have recognized a need in the art for improved systems and methods for preventing fraud in remote service inquiries in medical and other environments. The present application includes systems and methods for preventing fraud related to nurse triage services, but there are similar applications in other areas, such as any application including a teller discussing confidential information with a caller.

The present application addresses this issue by allowing callers to register only one device per profile. Each patient and the device may be approved prior to the patient being allowed to call the phone number associated with the nursing triage service, where the approval may come from physician or nurse triage service provider, from the paying party physician, or from the management care organization. When the caller uses that device, the teller is able to confirm that the register device is associated with the patient. The teller may able to confirm that the device is registered, and that the registered device is associated with the patient. The device-based nurse triage request described herein provides several advantages over existing solutions. The device-based nurse triage request provides an additional layer of security without requiring caller to identify the phone number. Additionally, the patient may specify the urgency of a nurse triage request, where an urgent call may require a response more quickly without making a phone call. The device-based nurse triage request also allows access to prepaid triage services (e.g., doctors, insurance, or Medicaid) without requiring a phone call to a nurse operator to verify the user against a membership directory. For example, existing solutions include a phone call to a nurse operator, where the fraud prevention requires the nurse operator to verify the identity of the caller and eligibility for the requested service submitting the request to a triage nurse. The device-based nurse triage request also allows access to paid medical triage services, also without requiring phone call to a nurse operator to verify the user against a membership directory. The device-based nurse triage request also allows for routing of the medical triage request, not just to a single medical services provider, but also to any nurse triage call center platform. The routing may be based on the triage request itself, such as the urgency of the request, a group to which the patient belongs, the current state, the time of day, or other routing factors. A patient may use an application on a mobile device to register a phone number. To reduce fraud, the system may require that each patient registers one telephone number. For additional security, the system may require that the phone number is associated with a smartphone that is running the application. When the patient enters his or her profile into a smartphone application, the profile is routed to the paying party for approval. Alternatively, the nurse triage service provider can upload a database of covered patient demographics from their practice management system (e.g., first name, last name, date of birth), so when the patient registers the mobile device application, the patient information can be confirmed automatically if they are in the database in the triage system. The databased is able to check that the person is on the database of approved patients. In some cases, the paying party may cover only a segment of their patients, such as patients over the age of 65.

Once the patient profile has been approved and associated with a phone number, then patient is allowed to request a nurse triage phone call directly from the application. The application will automatically provide the phone number associated with the smartphone, and the patient will only be able to enter the request if the phone number provided by the application matches the number originally registered with the nurse triage service provider. In some cases, the patient will be allowed to register only one phone number, and any change in phone numbers will render the old phone number invalid. There may be some exceptions, such as patients under the age of 18, that have more than one responsible person able to call for them. By requiring physician approval, patients may be prevented from sharing their nurse triage phone call service with other patients who are not covered by the paying party for the nurse triage service. In addition to requesting a call via a smartphone or a tablet, the patient may also request a call using a website entry page. Similarly, the patient will need to be pre-approved using a database that links the patients' names from the practice or corporate database of the covered patients.

This overview is intended to provide an overview of some of the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
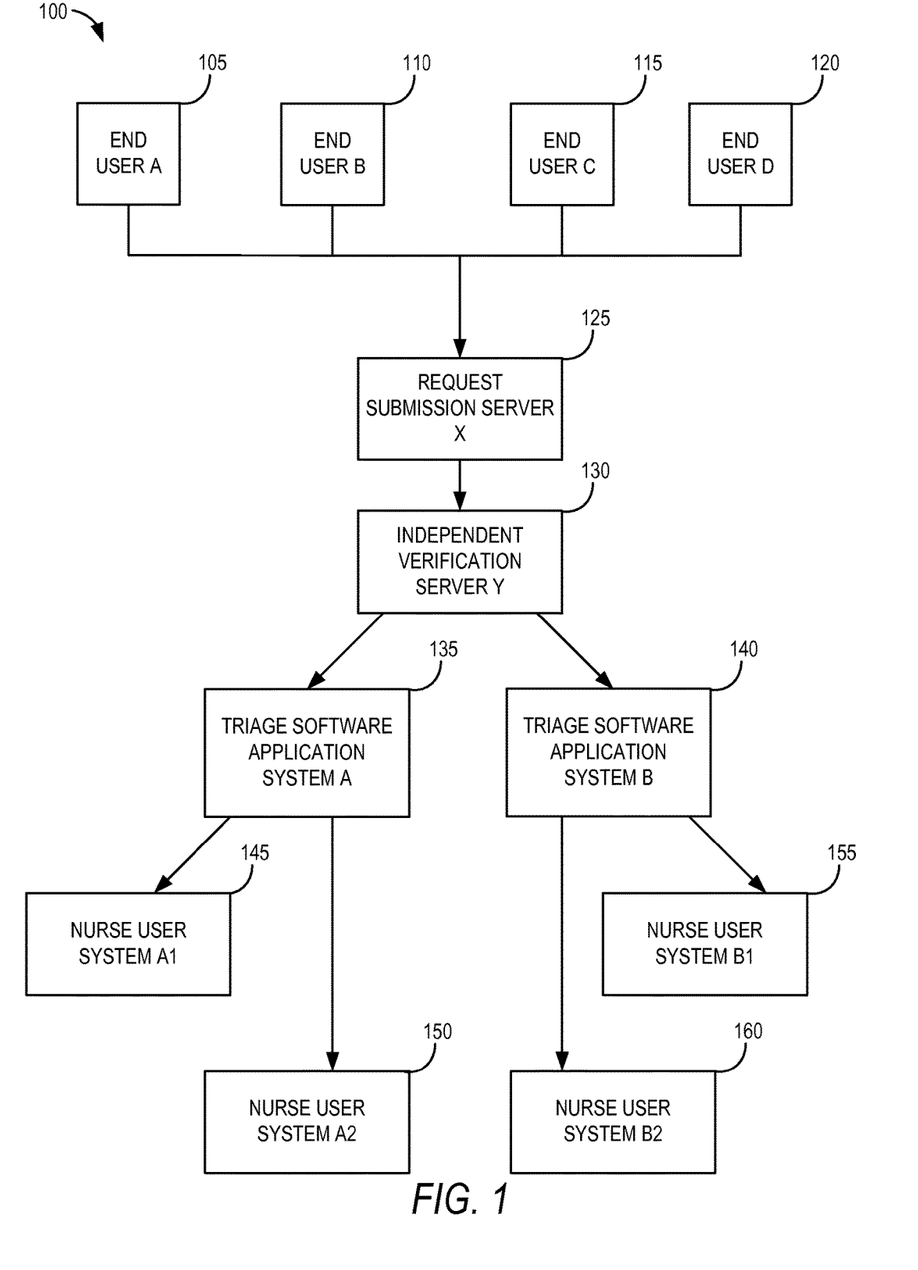
FIG. 1 is a block diagram illustrating generally an example of a routing nursing request originating from a mobile device.

FIG. 1 is a block diagram illustrating generally an example of a routing nursing request originating from a mobile device 100. The nursing request may be routed from one or more end users 105, 110, 115, and 120. Each end user may be associated with a mobile device, and may use the mobile device to submit a request to receive a call from a nurse. A user may submit a request to a request submission server 125. The request submission server 125 may forward the request to an independent verification server 130. The independent verification server 130 may be used to prevent fraud, such as by confirming that the request originated from the device associated with the user requesting a call. The independent verification server 130 may forward the request to one or more triage software application systems 135 and 140. Each triage software application systems 135 and 140 may be associated with one or more nurse user systems 145, 150, 155, 160, and may route the request to a particular nurse user system.

Figure 2:
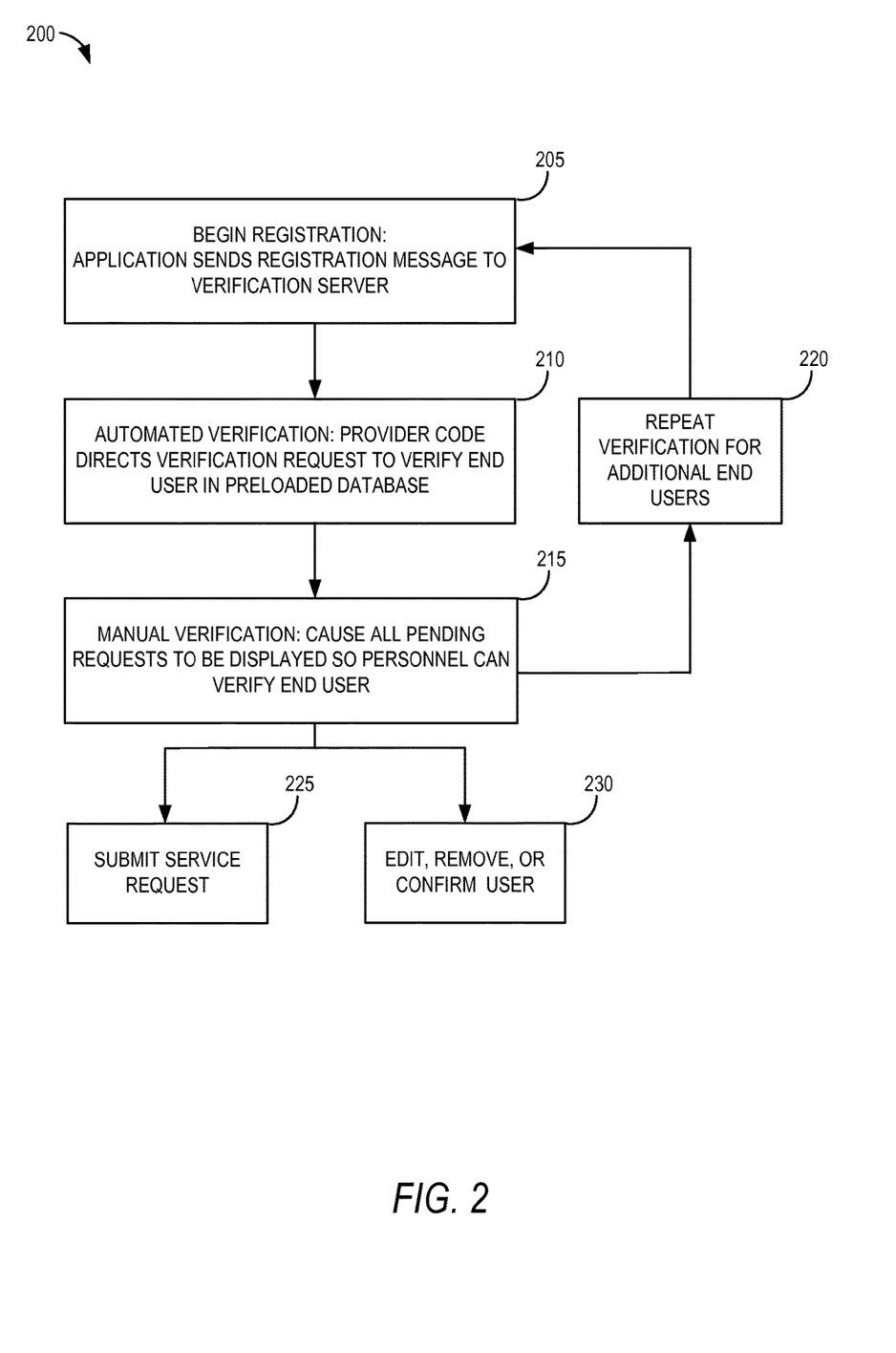
FIG. 2 is a block diagram illustrating generally an example of mobile device registration.

FIG. 2 is a block diagram illustrating generally an example of mobile device registration 200. A user may use a mobile application to begin registration 205. Registration begins with the application sending a registration message to a verification server. The registration message may be verified through an automated verification 210. The automated verification 210 may include using a provider code to direct the verification request to verify the user in a preloaded database. If the automated verification 210 is unable to verify the user, the registration may revert to a manual verification 215. The manual verification 215 may include causing all pending requests to be displayed so that medical personnel can verify an end user.

Once the user is verified automatically or manually, a unique verification code may be sent to the device. For example, the unique verification code may be an ASCII text string sent via short message service (SMS, or text messaging) sent to the SMS application residing on the mobile device. The unique verification code may be used to confirm the phone number of the device. For example, a user may use a smartphone to conduct the registration process over the internet (e.g., using internet protocol) and the unique verification code may be sent via SMS to confirm the phone number submitted during registration is associated with the smartphone used during registration. While many users will use the same device to complete the registration process and to receive phone calls, it may be possible to use a first device to complete registration and use a second device to receive the SMS verification code and to receive triage phone calls. For example, an internet tablet may be used to complete registration and a separate SMS-enabled phone may be used to receive the SMS verification code and to receive triage phone calls. Additionally, a combination of real or virtual devices may be used, such as virtual phone numbers (e.g., Google Voice) or virtual software environments.

A unique device identifier code may be used to identify the device uniquely. For example, a unique code may be generated upon downloading the mobile application, upon installing the application, upon sending the initial registration message to a verification server, or upon entering the text message confirmation code. The nurse triage service may associate the unique device identifier code and device with the user and with the user phone number. By associating the device with the user, the user may access the application and request a nurse triage call without having to place a separate call and without having to log into a web-based medical portal. A new installation of the software may generate a new unique device identifier code that may require registration of the new installation, and may result in de-registration of the previous device or phone number associated with the user.

Following verification of the user in the database and of the SMS unique verification code, the user may be prompted to enter a subscription code or payment. For example, a user may enter a prepaid code, a code associated with the user's health insurance provider (a group or individual number), or another subscription code. A user may be prompted to purchase a subscription, and may be provided with various subscription and payment options. For example, a user could make a one-time credit card payment for a single call, or may provide a credit card number to be used in an ongoing subscription.

If there are additional requests, the verification is repeated for all end users 220. Multiple users may be associated with a mobile device, such as registering parents and children within a single family. Multiple users is especially applicable for patients under the age of 18, as nurses may be required to have a guardian present whenever discussing or providing medical treatment to persons 18 or younger. A single user can register multiple people to be associated with a single device. For example, a user may pay for additional users, and for each additional user, a unique activation code may be generated. The mobile device may prompt the user to register multiple users at once, and may prompt the user to confirm insurance coverage or other payment for each user. For each request that is verified, the system may submit the service request 225. For reach request that cannot be verified, a system operator may be prompted to edit, remove, or confirm the user 230.

Figure 3:
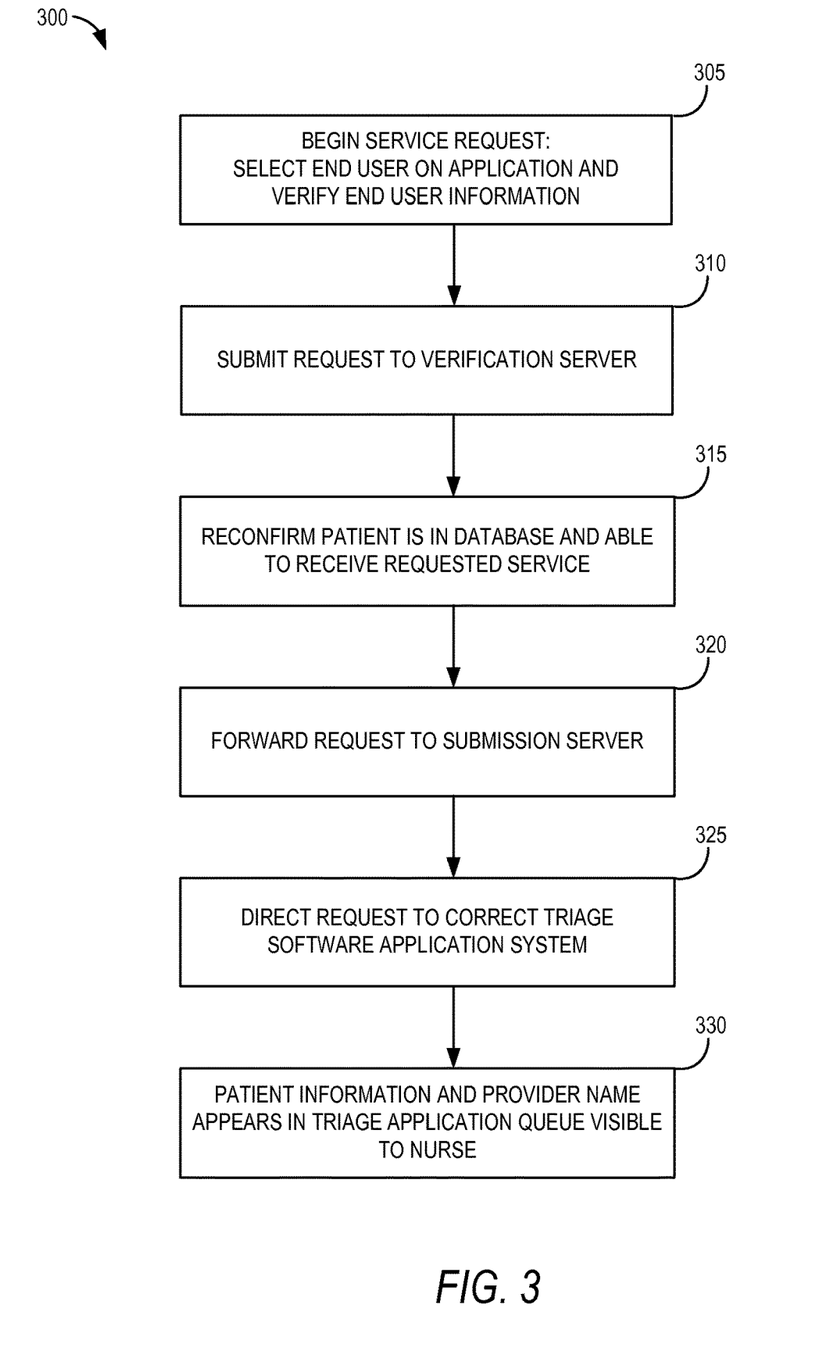
FIG. 3 is a block diagram illustrating generally an example of service request verification.

FIG. 3 is a block diagram illustrating generally an example of service request verification 300. The service request verification 300 may begin by selecting an end user on an application and verifying the end user information 305. Once the end user has been verified, the request may be send to the verification server 310. The verification server may reconfirm the patient is in the database and is able to receive the requested service 315. To verify the patient is in the database, the patent information may be forwarded with the request. One benefit of using a smartphone application to enter a request for a phone call or an appointment is that the basic caller information will already be sent along with the request from the application. For example, the smartphone application may send information pertinent to that particular transaction, such as gender, age, or credit card information. This information can be entered by the caller when registering for the application, and thereafter this information can be stored securely in the application and sent to the provider. To verify the patient is able to receive the requested service, the patient information may be verified against the services allowed for that patient. For example, the patient may be on a health services plan that pays for a predetermined number of service calls, or the patient may be required to pay for each service call. If the patient is required to pay for each service call, the service may determine whether the patient's account is funded or if credit can be extended to the patient. Once the patient information has been reconfirmed, the request may be forwarded to the submission server 320. From the submission server, the request may be directed to the correct triage software application system 325. Once received by the triage software application system, the patient information and provider name appears in the triage application queue visible to the nurse 330.

Mobile device registration 200 may be useful in preventing fraud in cases where the nurse triage service is paid by another party (e.g., Medicaid or a doctor), and may be useful in preventing fraud by customers that pay for the service directly. For example, patients may pay a fixed amount for a period, and may have the ability to submit an unlimited number of requests for the services of the nurse triage line. In some embodiments, patients may pay a base fee for the period, and may pay a minimal additional fee per service call. To prevent abuse, the requirement of having a single device per customer may prevent the customer from letting others use their account. To ensure only a single device is used per client, the system may send a unique prepaid code to their registered mobile number (e.g., via SMS message). The unique prepaid code may operate similar to the registration describe above, but the unique prepaid code may be unique to each prepaid user. Patients would be prevented from using unique prepaid code in multiple devices, as the unique prepaid code would be associated with a single phone number. The user may desire to change mobile devices, as is described with respect to FIG. 4.

Figure 4:
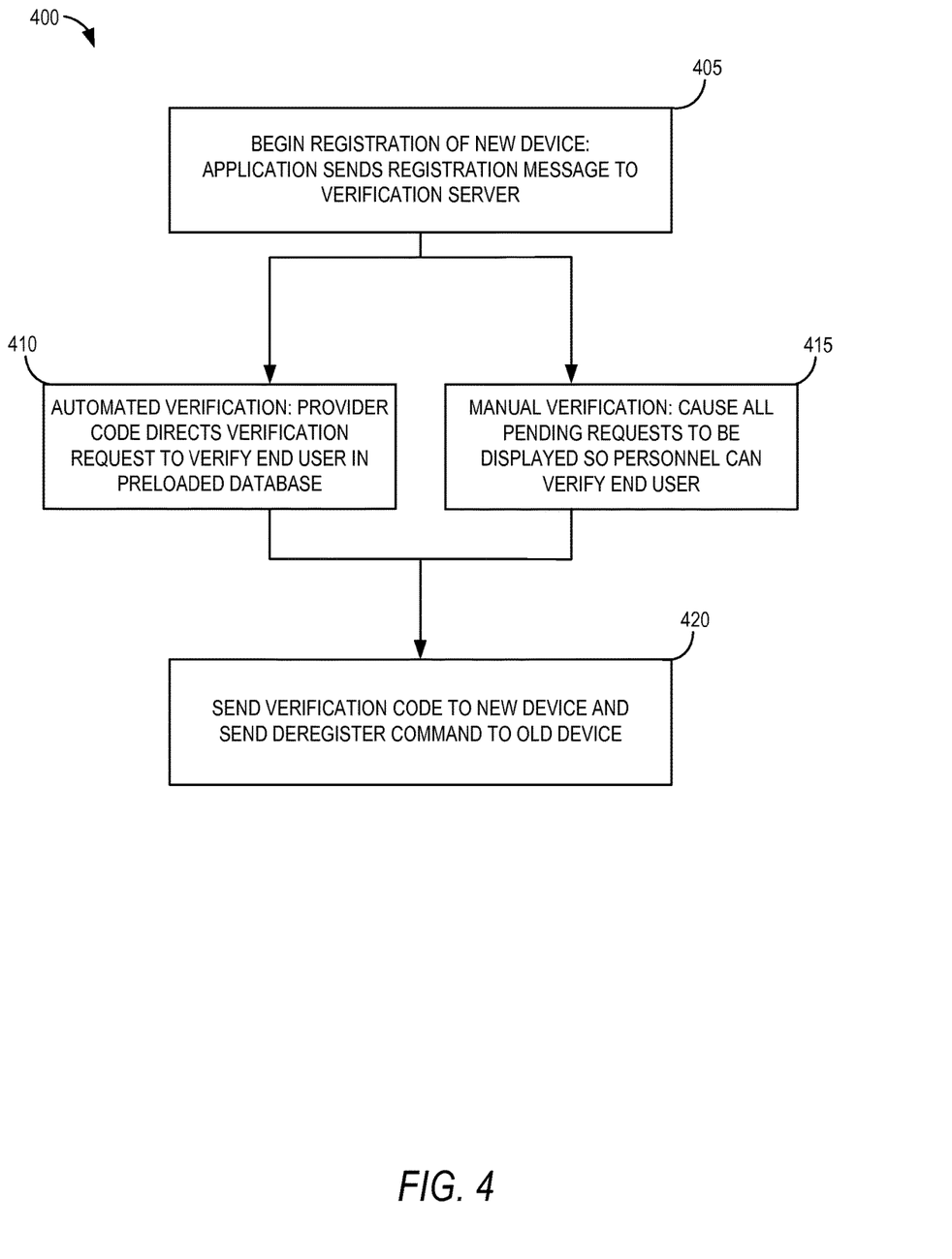
FIG. 4 is a block diagram illustrating generally an example of registration of a second mobile device.

FIG. 4 is a block diagram illustrating generally an example of registration of a second mobile device 400. Registration of a new mobile device may be desirable when a patient changes phones regardless of whether the patient retains the previous phone number. The user may use a mobile application to begin registration 405. Registration begins with the application sending a registration message to a verification server. The registration message may be verified through an automated verification 410. The automated verification 410 may include using a provider code to direct the verification request to verify the user in a preloaded database. If the automated verification 410 is unable to verify the user, the registration may revert to a manual verification 415. The manual verification 415 may include causing all pending requests to be displayed so that medical personnel can verify an end user. Once a request is verified, the system may send a verification code to the new device 420 and send a command to deregister the previous device. As described above, a unique verification code may be sent to the device, such as an ASCII text string sent via SMS. Additionally, installation of the software may generate a new unique device identifier code that may require registration of the new installation, and may result in de-registration of the previous device or phone number associated with the user. Because registration includes associating a new ID with the new device and phone number, the previous device is automatically deregistered when someone registers the new device. Registering a new device may automatically transfer any subscriptions associated with the user, or the user may be prompted to enter a new subscription code or payment.

Figure 5:
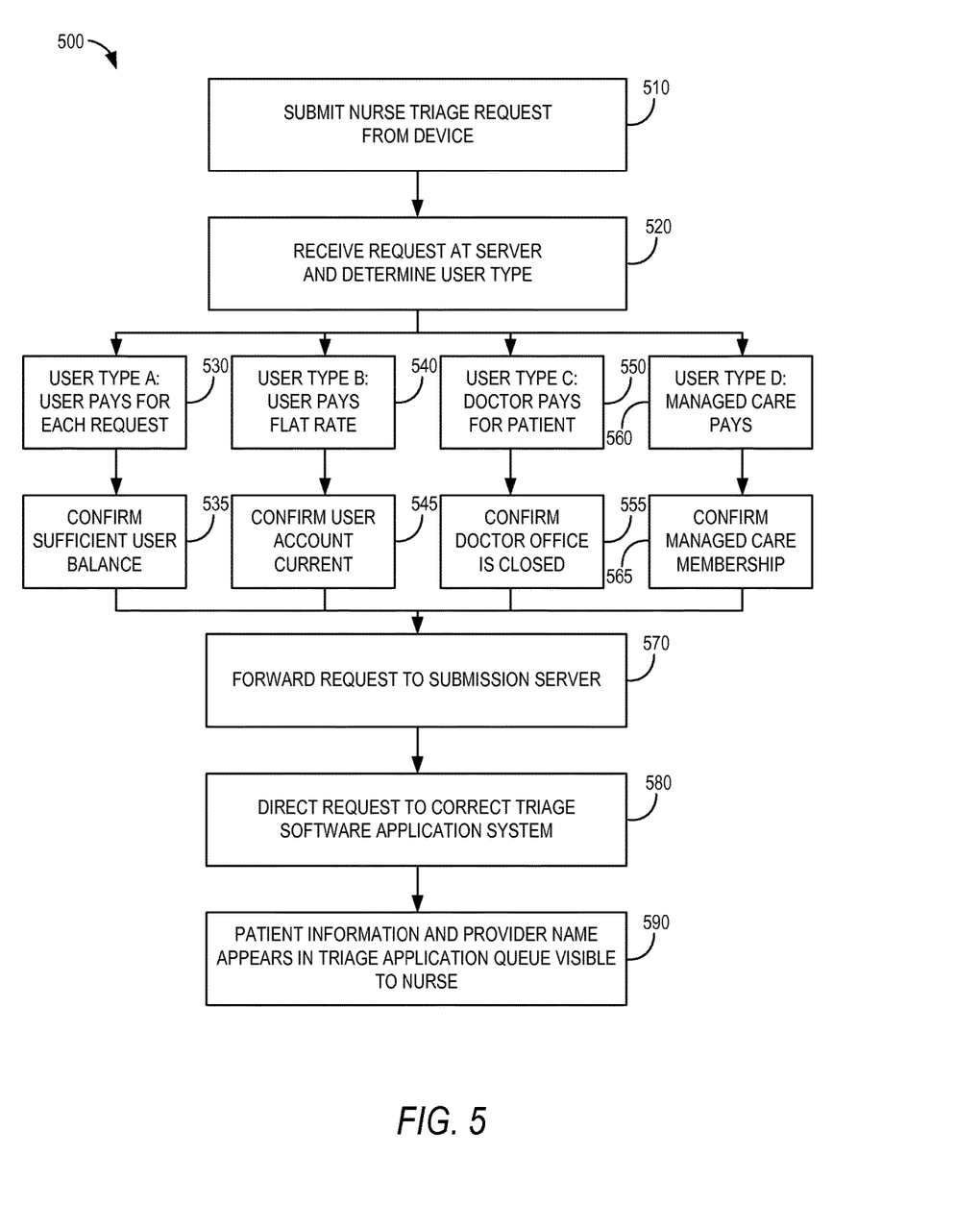
FIG. 5 is a block diagram illustrating generally an example of routing based on user type.

FIG. 5 is a block diagram illustrating generally an example of routing based on user type 500. The user may submit a request 510 from the application on the client device. The client device may have been previously registered as described above, and the request submission 510 may include the user entering login information on the client device or accessing the application without entering any login information. This may also include the user entering a username and password within a triage mobile device application or within a triage website being viewed on the mobile device. A user may be prompted to enter a description of the service being requested, such as a textual description of the reason for the request. Various information about the user may be displayed to the user for visual confirmation. For example, the user name, date of birth, and call back number may be presented to the user on the same screen as the textual description of the request reason. For devices on which multiple users are registered, this display may enable the user to confirm the name or phone number is associated with the intended person. Additionally, the information displayed to the user for confirmation may be locked from editing. For example, the user's name, date of birth, and phone number may be associated with each other. By preventing the user from changing the phone number, this may prevent a user from fraudulently requesting a call to a different number for a different person not covered by the subscription. A change in phone number may still be possible, but it may require either re-registering a device or calling the nurse triage service to confirm personally identifiable information and have an operator manually update a phone number. Once the request has been submitted 510, the application may display additional information, such as an expected wait time, the expected phone number or area code from which the triage call will originate, or a recommendation to call 911 or other numbers in the event of a medical emergency.

The request may be received 520 at a verification server to determine the user type. If the user has arranged to pay for each triage request 530, the user balance may be confirmed 535, and the request may be forwarded 570 to the triage request submission server. If the user has arranged to pay a flat rate for all triage requests 540, the user account may be confirmed as current 545, and the request may be forwarded 570. If the user's doctor has arranged to pay for the patient triage requests 550, the doctor office may be confirmed to be closed 565, and the request may be forwarded 570 to the triage request submission server. To reduce the costs associated with the use of the triage requests, if the doctor office is open, the request may be routed to the doctor office. If the user participates in a managed care system that pays for triage requests 560, the user managed care membership may be confirmed as current 565, and the request may be forwarded 570. Additional user types may be used to determine payment and request routing.

From the submission server, the request may be directed to the correct triage software application system 580. The request may be routed based on various considerations, such as the patient age, the patient gender, the patient type, the patient location, the time of day, the patient's health insurance provider, or other considerations. Once received by the triage software application system, the patient information and provider name appears in the triage application queue visible to the nurse 590.

For conceptual clarity, the above example has emphasized an embodiment that focuses on an inquiring party requesting medical attention from a call triage nurse. Of course, the answering service in the above example is not necessary, and the system can be applied to other uses in a medical environment, which may extend beyond requests for medical attention.

Various examples illustrate the systems and methods describe herein.

Example 1 includes a computer-assisted method of routing a nurse triage request without requiring a telephone call from a user to submit the nurse triage request, the method comprising registering a nurse triage request application residing on a mobile electronic device, receiving a nurse triage request from the registered nurse triage request application residing on the mobile electronic device, without requiring a telephone call from the user to submit the nurse triage request, verifying, in response to the received nurse triage request, that a user associated with the nurse triage request application residing on the mobile electronic device is authorized to submit the nurse triage request, and when the user has been verified as being authorized to submit the nurse triage request, routing the nurse triage request for fulfilling the nurse triage request.

Example 2 includes the method of example 1, wherein registering the nurse triage request application residing on the mobile electronic device includes receiving, via a first communication channel, an association request to associate the nurse triage request application residing on the mobile electronic device with the user, the association request including a mobile electronic device identifier uniquely associated with an installation of the nurse triage request application residing on the mobile electronic device, sending to the mobile electronic device, via a second communication channel, an association confirmation message code, the second communication channel being different from the first communication channel, receiving from the nurse triage request application residing on the mobile electronic device, via the first communication channel, the association confirmation message code, verifying that the user is authorized to submit the nurse triage request in response to receiving the association confirmation message code, and when the user has been verified as being authorized to submit the nurse triage request, associating the mobile electronic device identifier with the user to register the nurse triage request application residing on the mobile electronic device.

Example 3 includes the method of any of examples 1-2, wherein the first communication channel is an internet protocol communication channel, and the second communication channel is a short message service communication channel.

Example 4 includes the method of any of examples 1-2, wherein registering the nurse triage request application residing on the mobile electronic device further includes receiving payment information and a selection of a triage request routing service plan.

Example 5 includes the method of any of examples 1-2, wherein registering the nurse triage request application residing on the mobile electronic device further includes receiving a triage request plan code, the triage request plan code uniquely associated with a prepaid triage request routing service plan.

Example 6 includes the method of any of examples 1-2, wherein verifying that the user is authorized to submit the nurse triage request includes sending the association request to a remote authenticator device, and receiving, from the remote authenticator device, a confirmation that the user is authorized to submit the nurse triage request.

Example 7 includes the method of example 1, wherein the nurse triage call center server device platform includes a nurse triage queue, and wherein routing the nurse triage request includes routing the nurse triage request into the nurse triage queue.

Example 8 includes the method of any of examples 1-7, wherein routing the nurse triage request into the nurse triage queue includes determining whether the nurse triage request requires immediate attention, and when it is determined that the nurse triage request requires immediate attention, providing a notification to a nurse triage request service operator of the nurse triage request.

Example 9 includes the method of example 1, wherein routing the nurse triage request includes identifying a routing characteristic of the nurse triage request, and routing, based on the routing characteristic, the nurse triage request to a call center server device platform, the call center server device platform selected from among a plurality of available call center server device platforms.

Example 10 includes the method of any of examples 1-9, wherein the routing characteristic includes at least one of a patient age, a patient gender, a patient type, a patient location, a time of day, or a patient health insurance provider.

Example 11 includes the method of any of examples 1-10, wherein the patient type includes at least one of a user-paid triage request, a user-paid flat rate triage request, a doctor-paid triage request, or a managed care-paid triage request.

Example 12 includes the method of any of examples 1-2, wherein receiving the association request to associate the nurse triage request application residing on the mobile electronic device with the user includes receiving user identification information.

Example 13 includes the method of any of examples 1-12, wherein receiving user identification information includes receiving a name, a date of birth, and a social security number.

Example 14 includes the method of any of examples 1-12, wherein receiving user identification information includes receiving a unique health care provider identification number.

Example 15 includes a system for routing a nurse triage request without requiring a telephone call from a user to submit the nurse triage request, the system comprising a memory, a communication module, and a processor configured to register a nurse triage request application residing on a mobile electronic device, receive a nurse triage request from the registered nurse triage request application residing on the mobile electronic device, without requiring a telephone call from the user to submit the nurse triage request, verify, in response to the received nurse triage request, that a user associated with the nurse triage request application residing on the mobile electronic device is authorized to submit the nurse triage request, and when the user has been verified as being authorized to submit the nurse triage request, routing the nurse triage request for fulfilling the nurse triage request.

Example 16 includes the system of example 15, wherein, to register the nurse triage request application residing on the mobile electronic device, the processor is further configured to receive, via a first communication channel within the communications module, an association request to associate the nurse triage request application residing on the mobile electronic device with the user, the association request including a mobile electronic device identifier uniquely associated with an installation of the nurse triage request application residing on the mobile electronic device, send to the mobile electronic device, via a second communication channel within the communications module, an association confirmation message code, the second communication channel being different from the first communication channel, receive from the nurse triage request application residing on the mobile electronic device, via the first communication channel within the communications module, the association confirmation message code, verify that the user is authorized to submit the nurse triage request in response to receiving the association confirmation message code, and when the user has been verified as being authorized to submit the nurse triage request, associate the mobile electronic device identifier with the user to register the nurse triage request application residing on the mobile electronic device.

Example 17 includes the system of any of examples 15-16, wherein
the first communication channel within the communications module is an internet protocol communication channel, and the second communication channel within the communications module is a short message service communication channel.

Example 18 includes the system of any of examples 15-16, wherein, to register the nurse triage request application residing on the mobile electronic device, the processor is further configured to receive payment information and a selection of a triage request routing service plan.

Example 19 includes the system of any of examples 15-16, wherein, to register the nurse triage request application residing on the mobile electronic device, the processor is further configured to receive a triage request plan code, the triage request plan code uniquely associated with a prepaid triage request routing service plan.

Example 20 includes the system of any of examples 15-16, wherein, to verify that the user is authorized to submit the nurse triage request, the processor is further configured to send the association request to a remote authenticator device, and receive, from the remote authenticator device, a confirmation that the user is authorized to submit the nurse triage request.

Example 21 includes the system of example 15, wherein the nurse triage call center server device platform includes a nurse triage queue, and wherein the processor is further configured to route the nurse triage request includes routing the nurse triage request into the nurse triage queue.

Example 22 includes the system of any of examples 15-21, wherein, to route the nurse triage request into the nurse triage queue, the processor is further configured to determine whether the nurse triage request requires immediate attention, and when it is determined that the nurse triage request requires immediate attention, provide a notification to a nurse triage request service operator of the nurse triage request.

Example 23 includes the system of example 15, wherein, to route the nurse triage request, the processor is further configured to identify a routing characteristic of the nurse triage request, and route, based on the routing characteristic, the nurse triage request to a call center server device platform, the call center server device platform selected from among a plurality of available call center server device platforms.

Example 24 includes the system of any of examples 15-23, wherein the routing characteristic includes at least one of a patient age, a patient gender, a patient type, a patient location, a time of day, or a patient health insurance provider.

Example 25 includes the system of any of examples 15-24, wherein the patient type includes at least one of a user-paid triage request, a user-paid flat rate triage request, a doctor-paid triage request, or a managed care-paid triage request.

Example 26 includes the system of any of examples 15-30, wherein, to receive the association request to associate the nurse triage request application residing on the mobile electronic device with the user, the processor is further configured to receive user identification information.

Example 27 includes the system of any of examples 15-26, wherein receiving user identification information includes receiving a name, a date of birth, and a social security number.

Example 28 includes the system of any of examples 15-26, wherein receiving user identification information includes receiving a unique health care provider identification number.

Example 29 includes a computer-assisted method of routing a nurse triage request without requiring a telephone call from a user to submit the nurse triage request, the method comprising receiving a nurse triage request from a registered nurse triage request application residing on the mobile electronic device, without requiring a telephone call from the user to submit the nurse triage request, verifying, in response to the received nurse triage request, that a user associated with the nurse triage request application residing on the mobile electronic device is authorized to submit the nurse triage request, and when the user has been verified as being authorized to submit the nurse triage request, routing the nurse triage request for fulfilling the nurse triage request.

Example 30 includes the method of example 29, wherein verifying that the user is authorized to submit the nurse triage request includes sending the association request to a remote authenticator device, and receiving, from the remote authenticator device, a confirmation that the user is authorized to submit the nurse triage request.

Example 31 includes the method of example 29, wherein the nurse triage call center server device platform includes a nurse triage queue, and wherein routing the nurse triage request includes routing the nurse triage request into the nurse triage queue.

Example 32 includes the method of any of examples 29-31, wherein routing the nurse triage request into the nurse triage queue includes determining whether the nurse triage request requires immediate attention, and when it is determined that the nurse triage request requires immediate attention, providing a notification to a nurse triage request service operator of the nurse triage request.

Example 33 includes the method of example 29, wherein routing the nurse triage request includes identifying a routing characteristic of the nurse triage request, and routing, based on the routing characteristic, the nurse triage request to a call center server device platform, the call center server device platform selected from among a plurality of available call center server device platforms.

Example 34 includes the method of any of examples 29-33, wherein the routing characteristic includes at least one of a patient age, a patient gender, a patient type, a patient location, a time of day, or a patient health insurance provider.

Example 35 includes the method of any of examples 29-34, wherein the patient type includes at least one of a user-paid triage request, a user-paid flat rate triage request, a doctor-paid triage request, or a managed care-paid triage request.

Example 36 includes the method of example 29, wherein receiving the association request to associate the nurse triage request application residing on the mobile electronic device with the user includes receiving user identification information.

Example 37 includes the method of any of examples 29-36, wherein receiving user identification information includes receiving a name, a date of birth, and a social security number.

Example 38 includes the method of any of examples 29-36, wherein receiving user identification information includes receiving a unique health care provider identification number.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. In addition, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A computer-assisted method of routing a medical triage request, the method comprising:
   registering a medical triage request application residing on a user's mobile electronic device, the registration including:
      receiving an association request from the mobile electronic device at a verification server, the association request including a provider code uniquely associated with the mobile electronic device wherein the verification server includes:

a preloaded provider code database;
a medical triage request patient database including a plurality of patient entries, each patient entry corresponding to each of a plurality of managed patients within a medical practice management system; and
a unique device identification database;
verifying the provider code from the association request against the preloaded provider code database to confirm the user is authorized to register the medical triage request application; and
sending to the medical triage request application on the mobile electronic device an association confirmation message code in response to the confirmation that the user is authorized to register the medical triage request application; and
authorizing a medical triage request received from the mobile electronic device the authorization including:
receiving a medical triage request and a unique device identifier code at the verification server from the user through the registered medical triage request application residing on the mobile electronic device, the registered medical triage request application verifying the user information prior to submitting the medical triage request;
comparing the received medical triage request and the unique device identifier code to the plurality of patient entries within the medical triage request patient database, the comparison indicating that the user associated with the medical triage request application residing on the mobile electronic device is authorized to submit the medical triage request and identifying a patient type associated with the user; and
when the comparison identifies a match between the unique device identifier code and the plurality of entries within the medical triage request patient database and the user has been verified as being authorized to submit the medical triage request, routing the medical triage request based on the patient type to a triage software application system for fulfilling the medical triage request.

2. The method of claim 1, wherein:
the association request is received via a first communication channel;
the provider code is uniquely associated with an installation of the medical triage request application residing on the mobile electronic device to allow a single mobile electronic device to be registered at a time;
the association confirmation message code is sent to the mobile electronic device via a second communication channel, the second communication channel being different from the first communication channel; and
the association confirmation message code is received from the medical triage request application residing on the mobile electronic device via the first communication channel.

3. The method of claim 2, wherein:
the first communication channel is an internee protocol communication channel; and
the second communication channel is a short message service communication channel.

4. The method of claim 2, wherein registering the medical triage request application residing on the mobile electronic device further includes receiving payment information and a selection of a triage request routing service plan.

5. The method of claim 2, wherein registering the medical triage request application residing on the mobile electronic device further includes receiving a triage request plan code, the triage request plan code uniquely associated with a prepaid triage request routing service plan.

6. The method of claim 2, wherein verifying that the user is authorized to submit the medical triage request includes:
sending the association request to a remote authenticator device; and
receiving, from the remote authenticator device, a confirmation that the user is authorized to submit the medical triage request.

7. The method of claim 1, wherein:
the medical triage call center server device platform includes a medical triage queue; and
wherein routing the medical triage request includes routing the medical triage request into the medical triage queue.

8. The method of claim 7, wherein routing the medical triage request into the medical triage queue includes:
determining whether the medical triage request requires immediate attention; and
when it is determined that the medical triage request requires immediate attention, providing a notification to a medical triage request service operator of the medical triage request.

9. The method of claim 1, wherein routing the medical triage request includes:
identifying a routing characteristic of the medical triage request; and
routing, based on the routing characteristic, the medical triage request to a call center server device platform, the call center server device platform selected from among a plurality of available call center server device platforms.

10. The method of claim 9, wherein the routing characteristic includes at least one of a patient age, a patient gender, a patient type, a patient location, a time of day, or a patient health insurance provider.

11. The method of claim 10, wherein the patient type includes at least one of a user-paid triage request, a user-paid flat rate triage request, a doctor-paid triage request, or a managed care-paid triage request.

12. The method of claim 2, wherein receiving the association request to associate the medical triage request application residing on the mobile electronic device with the user includes receiving user identification information.

13. The method of claim 12, wherein receiving user identification information includes receiving a name and a date of birth.

14. The method of claim 12, wherein receiving user identification information includes receiving a unique health care provider identification number.

15. A verification server system for routing a medical triage request, the verification server system comprising:
a memory;
a communication module;
a preloaded provider code database;
a medical triage request patient database including a plurality of patient entries, each patient entry corresponding to each of a plurality of managed patients within a medical practice management system;
a unique device identification database; and
a processor configured to:
register a medical triage request application residing on a user's mobile electronic device, the registration including the processor being further configured to:

receive an association request from the mobile electronic device at the verification server, the association request including a provider code uniquely associated with the mobile electronic device;

verify the provider code from the association request against the preloaded provider code database to confirm the user is authorized to register the medical triage request application; and send to the medical triage request application on the mobile electronic device an association confirmation message code in response to the confirmation that the user is authorized to register the medical triage request application; and authorize a medical triage request received from the mobile electronic device, the authorization including the processor being further configured to:

receive a medical triage request and unique device identifier code at the verification server from the user through the registered medical triage request application residing on the mobile electronic device, the registered medical triage request application verifying the user information prior to submitting the medical triage request;

comparing the received medical triage request and the unique device identifier code to the plurality of patient entries within the medical triage request patient database, the comparison indicating that the user associated with the medical triage request application residing on the mobile electronic device is authorized to submit the medical triage request and identifying a patient type associated with the user; and when the comparison identifies a match between the unique device identifier code and the plurality of entries within the medical triage request patient database and the user has been verified as being authorized to submit the medical triage request, routing the medical triage request based on the patient type to a triage software application system for fulfilling the medical triage request.

16. The system of claim 15, wherein:

the association request is received via a first communication channel;

the provider code is uniquely associated with an installation of the medical triage request application residing on the mobile electronic device to allow a single mobile electronic device to be registered at a time;

the association confirmation message code is sent to the mobile electronic device via a second communication channel within the communications module, the second communication channel being different from the first communication channel; and the association confirmation message code is received from the medical triage request application residing on the mobile electronic device via the first communication channel within the communications module.

17. The system of claim 15, wherein, to route the medical triage request, the processor is further configured to:

identify a routing characteristic of the medical triage request; and route, based on the routing characteristic, the medical triage request to a call center server device platform, the call center server device platform selected from among a plurality of available call center server device platforms.

18. The system of claim 16, wherein, to verify that the user is authorized to submit the medical triage request, the processor is further configured to:

send the association request to a remote authenticator device; and receive, from the remote authenticator device, a confirmation that the user is authorized to submit the medical triage request.

19. The system of claim 15, wherein the medical triage call center server device platform includes a medical triage queue, and wherein the processor is further configured to route the medical triage request includes routing the medical triage request into the medical triage queue.

20. The system of claim 19, wherein, to route the medical triage request into the medical triage queue, the processor is further configured to determine whether the medical triage request requires immediate attention, and when it is determined that the medical triage request requires immediate attention, provide a notification to a medical triage request service operator of the medical triage request.

* * * * *

UNITED STATES PATENT AND TRADEMARK OFFICE
CERTIFICATE OF CORRECTION

PATENT NO. : 10,510,130 B2
APPLICATION NO. : 14/610520
DATED : December 17, 2019
INVENTOR(S) : Raheja et al.

Page 1 of 1

It is certified that error appears in the above-identified patent and that said Letters Patent is hereby corrected as shown below:

In the Claims

In Column 12, Line 66, in Claim 1, delete "device" and insert --device,-- therefor In Column 13, Line 19, in Claim 1, delete "device" and insert --device,-- therefor In Column 13, Line 60, in Claim 3, delete "internee" and insert --internet-- therefor Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*